United States Patent [19]

Holmes

[11] Patent Number: 4,755,182
[45] Date of Patent: Jul. 5, 1988

[54] REDUCED GLARE INTRAOCULAR LENS

[75] Inventor: Charles J. Holmes, Rialto, Calif.

[73] Assignee: Iolab Corporation, Claremont, Calif.

[21] Appl. No.: 851,832

[22] Filed: Apr. 14, 1986

[51] Int. Cl.⁴ .............................................. A61F 2/16
[52] U.S. Cl. ...................................................... 623/6
[58] Field of Search ............................................. 623/6

[56] References Cited

U.S. PATENT DOCUMENTS

| 4,159,546 | 7/1979 | Shearing | 623/6 |
| 4,298,994 | 11/1981 | Clayman | 623/6 |
| 4,316,292 | 2/1982 | Alexeev | 623/6 |
| 4,418,431 | 12/1983 | Faster | 623/6 |

OTHER PUBLICATIONS

Medical Optics PC-156 Lens Style Sheet, Oct. 1983.

Primary Examiner—Richard J. Apley
Assistant Examiner—James Prizant
Attorney, Agent, or Firm—Donal B. Tobin

[57] ABSTRACT

A low glare intraocular lens optic using partial depth positioning holes.

10 Claims, 4 Drawing Sheets

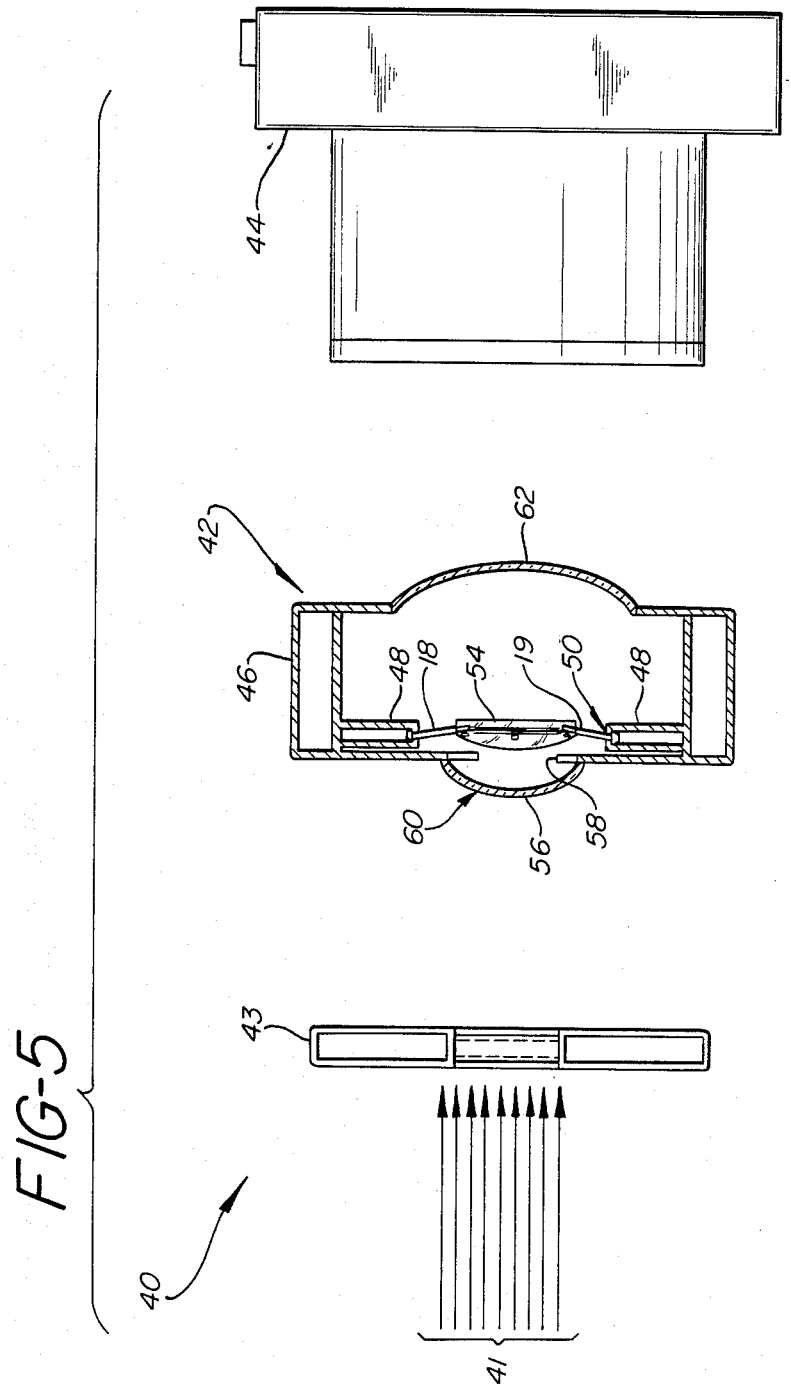

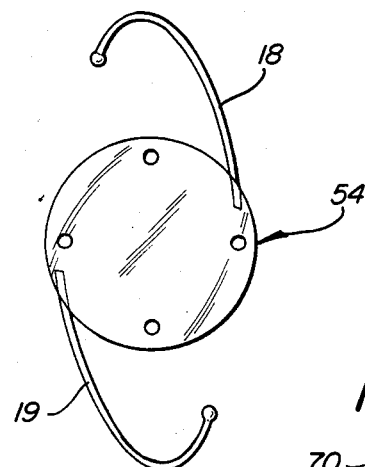
FIG-6A PRIOR ART
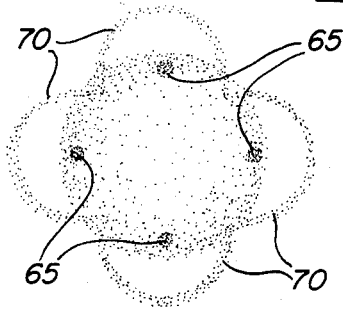
FIG-6B PRIOR ART
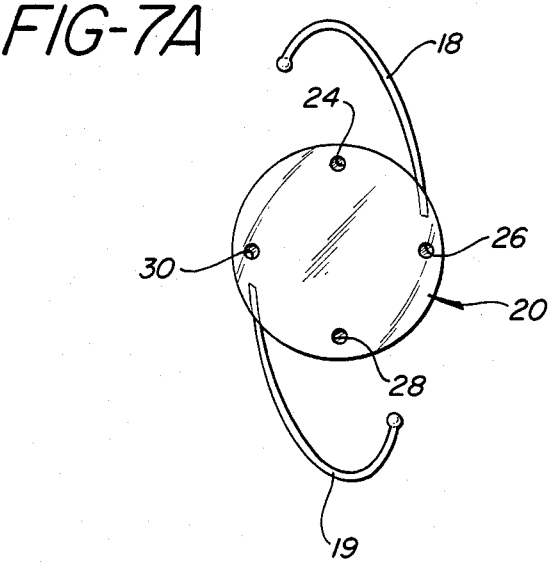
FIG-7A
FIG-7B
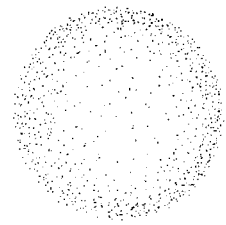

REDUCED GLARE INTRAOCULAR LENS

FIELD OF THE INVENTION

The present invention relates to the optic for an intraocular lens and more particularly to a reduced glare intraocular lens using positioning holes extending only part way through the optic.

BACKGROUND OF THE INVENTION

It is now commonly accepted that the vision imparing disease known as cataracts can be alleviated by surgically replacing the natural lens of the eye with an artificial intraocular lens.

The anatomy of the eye 1 is shown schematically in FIG. 1B. The cornea 2 forms the front surface of the eye and connects with the ciliary muscle 3 from which the iris 4 extends. Iris 4 divides the front portion of the eye into the anterior chamber 5 between the iris 4 and the cornea 2 and the posterior chamber 6 behind the iris. Pupil 8 is the aperture in the center of the iris through which light passes to the posterior chamber and to the back of the eye (not shown). Pupil 8 enlarges and contracts as iris 4 changes size in response to light impinging upon the iris tissue. The natural lens of the eye (not shown) is removed during cataract surgery leaving, in certain circumstances, the capsular bag 10 in place. Suspensary ligaments 12, also known as zonules support capsular bag 10 in posterior chamber 6 of the eye extending from the periphery of capsular bag 10 to the surrounding ciliary muscle 3.

An intraocular lens may be inserted in the eye by a variety of well known surgical techniques. A representative intraocular lens is shown in the eye in FIGS. 1A and 1B. An intraocular lens has two principal parts: a medial light-focusing body 20 (also called the optic) made of non-toxic plastic material which will replace the natural lens of the eye and focus light on the retina: and haptic support portions 18, 19 which extend from optic 20 to the anatomy of the eye and provide a means for fixing and holding optic 20 in its proper position within the eye.

Many surgical procedures of choice require that the lens be manipulated during the insertion. In the past positioning holes 14 have been used for that purpose. A surgical instrument 15, often called a hook, is inserted through an incision 16 into the eye. The end of the hook is placed into hole 14 which in the past has been drilled completely through optic 20 generally in a direction parallel to the optical axis of optic 20. Once hook 15 is inserted into positioning hole 14, the lens may be maneuvered as desired by the surgeon.

It has been found that positioning holes of intraocular lens optics cause certain amount of glare and glitter. This is particularly troublesome during the evening when the iris of the eye is open to a larger extent than it is during the day and consequently the pupil 8 is larger than usual. Thus, at night, even when the lens is placed in posterior chamber 6 behind iris 4, the positioning holes can be in the path of light between the cornea and retina. It would be desirable to have an intraocular lens which provided positioning holes for the use of the surgeon during insertion of the lens but on which the positioning holes did not cause additional glare and glitter for the patient after the lens is inserted.

SUMMARY OF THE INVENTION

The present invention provides a lens which has positioning holes for use of the surgeon during insertion of the lens but I have found that the positioning holes of the present invention significantly reduce glare and glitter during use of the lens particularly in night vision. Conventional positioning holes have always been drilled completely through the lens and the anterior of the holes has been highly polished to match the finish of the remainder of the lens. I have found that drilling part way through the lens and not polishing the interior surface of the hole reduces glare significantly.

The present invention includes an optic with a central optical zone and a peripheral zone integral with and circumferentially surrounding the central optical zone. The peripheral zone includes the peripheral edge of the lens. The lens includes at least one positioning hole located in the peripheral zone and extending only partway into the anterior face of the lens toward the posterior face. Any desirable number of positioning holes may be included in the lens. I prefer to leave the interior surface of the holes unpolished so that it has a generally frosted appearance. I have found that this reduces glare and glitter.

I also prefer to leave the bottom of the positioning hole reasonably flat rather than triangular shaped. The flat bottom is obtained by using an end mill or a shallow angle twist drill rather than a conventional twist drill to make the hole.

These and other features and advantages of the present invention will become more apparent when taken in conjunction with the following detailed description of the preferred embodiments and the following drawings.

BRIEF DESCRIPTION OF THE DRAWINGS

FIG. 5 shows a laboratory eye model used to evaluate glare in an intraocular lens;

FIG. 6A shows a lens with full depth positioning holes;

FIG. 6B shows a schematic representation of the glare from the lens of FIG. 6A when it is placed in the eye model of FIG. 5;

FIG. 7A shows a lens with partial depth positioning holes; and

FIG. 7B shows a schematic representation of the glare from the lens of FIG. 7A when it is placed in the eye model of FIG. 5.

DETAILED DESCRIPTION OF THE PREFERRED EMBODIMENT

Figure 2:
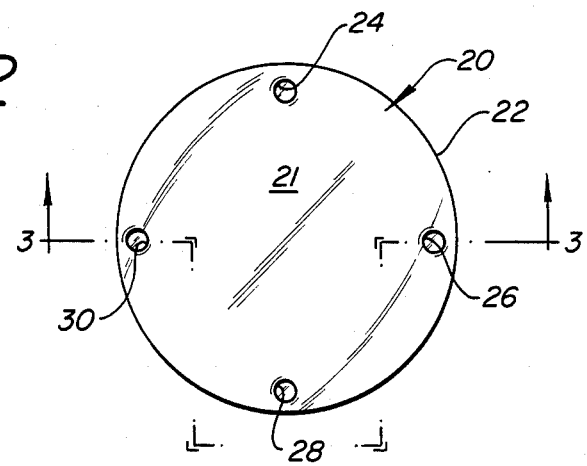
FIG. 2 shows a plan view of the anterior surface of an intraocular lens.

Referring now to FIG. 2 there is shown an intraocular lens 20 having a circumferential edge 22 and having four positioning holes 24, 26, 28, and 30 extending only partway into the anterior surface 21 and not all the way through the lens 20.

Figure 1A:
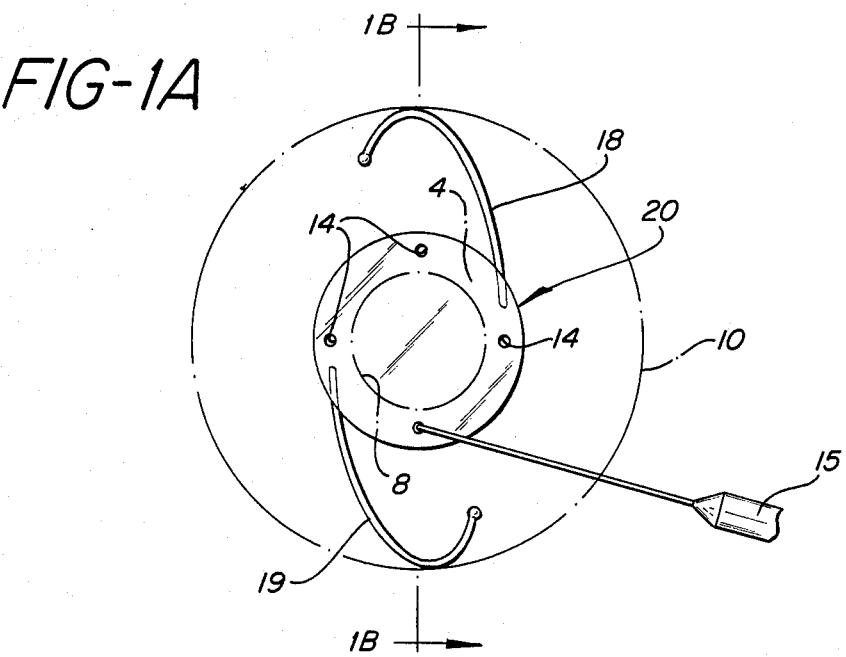
FIG. 1A shows a schematic front view of the anatomy of the eye.
Figure 1B:
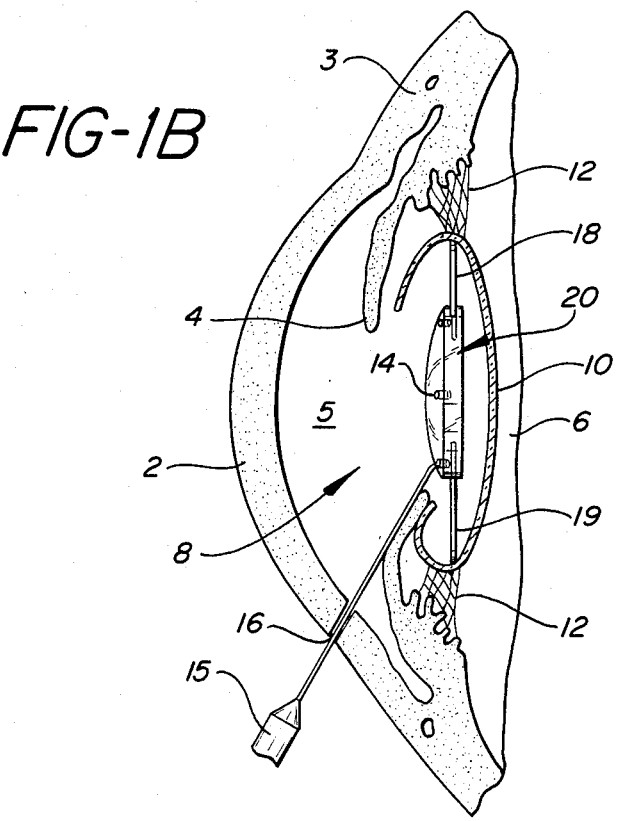
FIG. 1B shows a schematic side cross section view of the anatomy of the eye taken along line 1B—1B in FIG. 1A.
Figure 3:
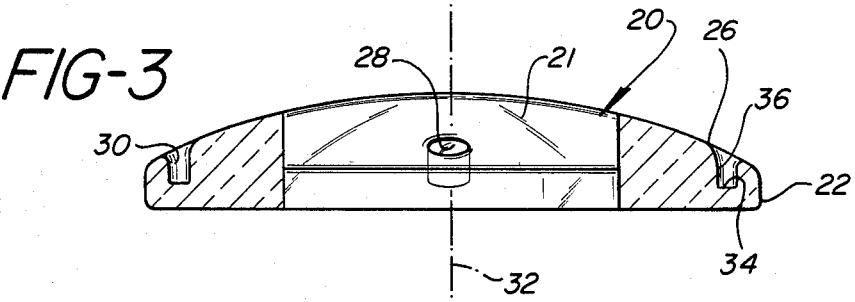
FIG. 3 shows a side elevational view, shown partly in section, of an intraocular lens taken along line 3—3 and FIG. 2.

As can be seen from FIG. 3, which is a side elevational view, shown partly in section, of the lens shown in FIG. 2 positioning holes 24, 26, 28 and 30 extend only partway into lens 20 from anterior surface 21 in a direction generally parallel to the optical axis 32 of lens 20. In the preferred embodiment, the depth of each positioning hole 24, 26, 28 and 30 extends about halfway through the optic in a direction measured parallel to the optical axis 32 as shown in FIG. 3. This allows the lens to be securely held and easily manipulated by a hook inserted into the positioning hole as shown in FIG. 1. The diameter of all of the positioning holes 26–30 is a standard diameter similar to full depth positioning holes on prior art lenses. The bottom 34 of positioning holes 24–30 is preferably flat and generally perpendicular to the axis of the positioning hole. Alternatively, bottom 34 may not be perfectly flat but may have a convex or concave curvature on a slightly conical convexity or concavity depending on the tool used to make the hole. The important feature of bottom 34 is that it should be aligned so that incoming light impinging upon bottom 34 is not reflected back to the retina.

Figure 3A:
FIG. 3A shows a partial sectional view of an intraocular lens.

Alternatively, as shown in FIG. 3A, positioning hole 30' extends in a direction generally perpendicular to the adjacent anterior surface 21 of the lens. Since, for a convex anterior surface 21, positioning hole 30' extends away from the edge of optic 20, positioning hole 30' may be placed closer to the edge of optic 20 and thus, farther from the central optical zone of optic 20.

Figure 4A:
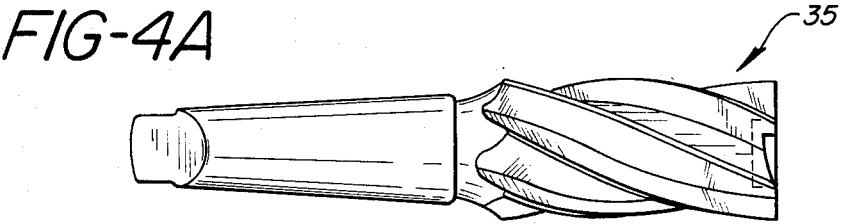
FIGS. 4A and 4B show the tool used to make the positioning holes in the lens of FIG. 2.
Figure 4B:
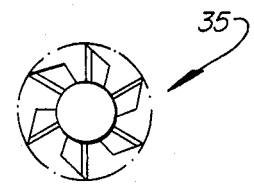

As can be seen from FIGS. 4A and 4B positioning hole 26 is drilled with a conventional end mill 35 which has a generally cylindrical shaft and a generally flat but slightly convex base. I have also found that a shallow angle twist drill with a base angle of about 2½° leaves a slight conical depression in the base of positioning holes 24–30 and that this is acceptable. Other angles would also be acceptable as long as appreciable light was not reflected off the angled surface back to the retina.

The interior circumference 36 of positioning holes 24–30 is not polished to any significant degree so it is left with a frosted appearance that it receives during the drilling procedure. This frosted interior circumference of positioning holes 24–30 helps diffuse light impinging upon the positioning hole to further reduce glare. The generally flat bottom 34 of positioning holes 24–30 also has a frosted appearance to reduce glare and its alignment perpendicular to the axis of positioning holes 24–30 and generally perpendicular to the optical axis of lens 20 helps reduce the chance of reflecting undesired light onto the retina. The entry area of each positioning hole 24–30 is rounded to avoid sharp edges and to further reduce glare.

The Gullstrand eye model 40 shown in FIG. 5 can be used to compare the amount of glare from full depth positioning holes of a conventional intraocular lens with partial depth positioning holes of the present invention. In eye model 40, a beam of collimated white light 41 is passed through a variable diaphragm 43 through a device for simulating the optics of the eye 42 and then to a camera 44 which sees the light as it comes through the eye 42.

Eye simulator 42 is a generally cylindrical housing 46 with an annular lens holder 48 projecting inwardly from the interior wall of housing 46 and having a groove 50 into which haptic loops 18 and 19 extend to hold an intraocular lens 54 in place. The face of the eye simulator 42 which faces the collimated light beam 41 will be called the corneal face 56 a corneal lens 60 to simulate the cornea of the eye. Variable diaphragm 58 simulates the iris of the eye. The surface 62 of housing 46 which faces camera 44 will be called the retinal surface. The exterior of retinal surface 62 is frosted to act as a projection screen onto which light falls after it has passed through lens 54.

Retinal surface 62 has a curvature which is representative of the curvature of the retina. Eye simulator 42 is dimensioned to approximate the dimensions of a human eye. The space between the corneal face 56 and the retinal surface 62 is filled with saline solution to approximate the anatomy of the eye.

A camera 44 can be a still camera with a high speed film, for example, 400 ASA film which is red sensitive. One could also use a video camera to provide a moving picture of the light coming through eye simulator 42. The camera 44 is focused on retinal surface 62 so that one can record the image that is projected through lens 54 onto the retinal surface of 62 of eye simulator 42.

In a first test, a conventional intraocular lens 54 shown in FIG. 6A having a 6 millimeter diameter and with full depth positioning holes was placed in eye simulator 42 with haptic loops 18, 19 held in position in groove 50. Variable aperture 58 was closed to a diameter less than the diameter of the lens 54 and less than the diameter of the circle whose circumference included the four positioning holes. Variable diaphragm 43 was closed to a diameter less than the diameter of the circle which included the four positioning holes of lens 54. A beam of collimated white light 41 was projected through variable diaphragm 43, corneal lens surface 56, lens 54 in a direction generally parallel to the optical axis of lens 54, onto retinal surface 62 and photographed by camera 44. This was a test specimen used to give an no glare equivalent.

In a second test the same lens was left in eye simulator 42 variable diaphragm 43 was opened up to a diameter greater than the diameter of lens 54 (for example, 7 millimeters) and variable aperture 58 was opened to a diameter greater than the diameter of the circle whose circumference included the four full depth positioning holes of lens 54 (for example, 7 millimeters) and light was projected in a direction generally parallel to the optical axis of lens 54 on the retinal surface 62 and photographed by camera 44. As shown in the schematic representation in FIG. 6B, each full depth positioning hole in lens 54 created a light tube 65 for unfocused light which was projected directly on the retina. Also, each full depth positioning hole created a halo effect 70 showing four rings of light generated by the full depth positioning holes. This test simulates the human eye when the iris is open wide in a dark room or at night.

A third test was conducted in which variable diaphragm 43 and variable aperture 58 were left in the same position as with test #2 above, but an intraocular lens 20 which had four partial depth positioning holes 24, 26, 28 and 30 (see FIG. 7A) was inserted in place of lens 54. These partial depth positioning holes were fully exposed to the beam of collimated white light 41.

FIG. 7B shows a schematic representation of the lack of glare that was experienced with partial depth positioning holes. First, there are no light tubes to carry unfocused light straight through the positioning hole to the retina. Furthermore, there are only very faint halos 72 which is believed to be due to slight reflections from the edge of the lens, not the partial depth positioning holes.

It is therefore believed that the present invention provides a intraocular lens with substantially reduced glare.

The present invention has been described in conjunction with preferred embodiment. Those skilled in the art will appreciate that many modifications and changes may be made to the preferred embodiments without departing from the present invention. It is, therefore, not intended to limit the present invention except as set forth in the appended claims.

I claim:

1. An optic for an intraocular lens having an optical axis, having an anterior face intersecting said optical axis, having a posterior face intersecting said optical axis and spaced apart from said anterior face along said optical axis and a surrounding peripheral edge comprising:
   a central optical zone;
   a peripheral zone integral with and circumferentially surrounding said central optical zone and including said peripheral edge;
   at least one positioning hole located in said peripheral zone and extending about half way through said optic in a direction measured parallel through said optical axis from said anterior face toward said posterior face;
   wherein the interior surface of said at least one positioning hole receives no polishing and is left substantially in the condition left by the tool which makes the hole; and,
   wherein the base of said hole forms an angle which is approximately perpendicular to the optical axis.

2. The optic of claim 1 wherein said at least one positioning hole projects in a direction generally parallel to said optical axis.

3. The optic of claim 1 wherein the anterior face is convex.

4. The optic of claim 1 wherein the posterior face is planar.

5. The optic of claim 1 wherein the circumferential edge of said optic is circular.

6. The optic of claim 1 wherein said at least one positioning hole includes two positioning holes equi-angularly spaced about said optic.

7. The optic of claim 1 wherein said at least one positioning hole includes four positioning holes equi-angularly spaced about said optic.

8. The optic of claim 1 wherein the base of said hole forms a slight conic depression said cone having a base angle in the range of 0°–10°.

9. The optic of claim 1 wherein said at least one positioning hole projects in a direction generally perpendicular to said anterior face.

10. An optic for an intraocular lens having an optical axis, an anterior face intersecting said optical axis, a posterior face intersecting said optical axis and spaced apart from said anterior face along said optical axis, and a surrounding peripheral edge comprising:
   a central optical zone;
   a peripheral zone integral with and circumferentially surrounding said central optical zone and including said peripheral edge;
   at least one positioning hole located in said peripheral zone and extending at least half but less than all the way through said optic in a direction measured parallel to said optical axis from said anterior face toward said posterior face, wherein the base of said hole forms an angle which is approximately perpendicular to the optical axis, and wherein at least the base of the hole is left unpolished.

* * * * *